(12) United States Patent
Brosda et al.

(10) Patent No.: US 6,355,151 B1
(45) Date of Patent: *Mar. 12, 2002

(54) GAS SENSOR

(75) Inventors: Susanne Brosda, Patras (GR); Ulrich Guth, Greifswald (DE); Silvia Lenaerts, Kuringen (BE); Götz Reinhardt, Böblingen; Ulrich Schönauer, Eggenstein, both of (DE)

(73) Assignee: Heraeus Electro-Nite International N.V., Houthalen (BE)

( * ) Notice: Subject to any disclaimer, the term of this patent is extended or adjusted under 35 U.S.C. 154(b) by 0 days.

This patent is subject to a terminal disclaimer.

(21) Appl. No.: 09/312,184

(22) Filed: May 14, 1999

Related U.S. Application Data

(63) Continuation of application No. PCT/EP98/05823, filed on Sep. 14, 1998.

(30) Foreign Application Priority Data

Sep. 15, 1997 (DE) .......................................... 197 40 500
Dec. 20, 1997 (DE) .......................................... 197 57 112

(51) Int. Cl.⁷ ............................................. G01N 27/407

(52) U.S. Cl. ...................... 204/424; 204/429; 205/784.5

(58) Field of Search ................................. 204/421–429

(56) References Cited

U.S. PATENT DOCUMENTS

| | | | | |
|---|---|---|---|---|
| 3,514,377 A | * | 5/1970 | Spacil et al. ................ | 204/427 |
| 4,101,403 A | * | 7/1978 | Kita et al. ................... | 204/429 |
| 4,145,272 A | | 3/1979 | Nakamura et al. | |
| 4,402,820 A | * | 9/1983 | Sano et al. .................. | 204/429 |
| 4,416,763 A | | 11/1983 | Bujishiro | |

(List continued on next page.)

FOREIGN PATENT DOCUMENTS

| | | |
|---|---|---|
| DE | 42 25 775 A1 | 2/1994 |
| DE | 195 34 918 A1 | 1/1997 |
| DE | 41 09 516 C2 | 8/1997 |
| EP | 0 335 666 A3 | 10/1989 |
| WO | WO 95/30146 | 11/1995 |
| WO | WO 96/17242 * | 6/1996 |

OTHER PUBLICATIONS

S. Bebelis and D. G. Vayenas, "Non–Faradaic Electrochemical Modification of Catalytic Activity", *J. of Catalysis*, 118, pp. 125–146 (1989).

(List continued on next page.)

*Primary Examiner*—T. Tung
(74) *Attorney, Agent, or Firm*—Akin, Gump, Strauss, Hauer & Feld, LLP

(57) ABSTRACT

A gas sensor is provided for measurement of oxygen and/or the air-to-fuel lambda ratio and hydrocarbons and/or carbon monoxide in gas mixtures. To reliably measure a plurality of gaseous components, the sensor is provided with a reference electrode representing a constant oxygen partial pressure, an oxygen ion-conducting solid electrolyte, and at least two measuring electrodes, the measuring electrodes and the reference electrode being mounted directly on the solid electrolyte and having electrical leads for connection and for take-away of electrical measurement signals. The solid electrolyte (1) is constructed with a measurement gas side exposed to the gas mixture and a reference gas side separated from the gas mixture. The system of electrodes has the reference electrodes (9; 9") on the reference gas side and at least two measuring electrodes (2; 2'; 2"; 3) on the measurement gas side, and is so constructed that one of the reference electrodes (9) is assigned to at least one measuring electrode (2), which forms the anode of this electrode pair (2, 9). The pair of electrodes (2, 9) is adapted for the application of a voltage or a current for pumping oxygen, and the system simultaneously transmits at least two measurement signals, which correspond to different gaseous components of the gas mixture.

3 Claims, 4 Drawing Sheets

U.S. PATENT DOCUMENTS

| | | | |
|---|---|---|---|
| 4,427,525 A | | 1/1984 | Lin et al. |
| 4,476,008 A | * | 10/1984 | Sano et al. ................. 204/429 |
| 4,502,939 A | * | 3/1985 | Holpelder et al. .......... 204/429 |
| 4,828,673 A | * | 5/1989 | Maeda ....................... 204/427 |
| 5,352,353 A | * | 10/1994 | Schonauer et al. ......... 204/426 |
| 5,397,442 A | * | 3/1995 | Wachsman .................. 204/428 |
| 5,460,711 A | | 10/1995 | Riegel et al. |
| 5,482,609 A | * | 1/1996 | Kobayashi et al. ......... 204/424 |

OTHER PUBLICATIONS

I.Y. Yentekakis, S. Neophytides and C.G. Vayenas, "Solid Electrolyte Aided Study of the Mechanism of CO Oxidation on Polycrystalline Platinum", *J. of Catalysis*, 111, pp. 152–169 (1989).

W.J. Fleming, "Physical Principles Governing Nonideal Behavior of the Zirconia Oxygen Sensor", J. Electrochem, Soc.: Electrochemical Sci. and Tech. 124:1 (Jan. 1997).

* cited by examiner

GAS SENSOR

CROSS REFERENCE TO RELATED APPLICATION

This application is a continuation of International Application PCT/EP98/05823, filed Sep. 14, 1998, the disclosure of which is incorporated herein by reference.

BACKGROUND OF THE INVENTION

The present invention relates to a gas sensor for measurement of oxygen and/or the air-to-fuel lambda ratio and hydrocarbons and/or carbon monoxide in gas mixtures. The gas sensor has a reference electrode representing a constant oxygen partial pressure, an oxygen ion-conducting solid electrolyte, and at least two measuring electrodes, the measuring electrodes and the reference electrode being mounted directly on the solid electrolyte and having electrical leads for connection and for take-away of the electrical measurement signals. The invention also relates to applications for the gas sensor and to a measurement method.

A gas sensor of a this type is known, e.g., from German published patent application DE 195 34 918 A1. The sensor therein has two electrodes constructed as mutually engaging comb structures (see FIG. 1), which are arranged on the side of the solid electrolyte facing the gas being measured (hereinafter "measurement gas"), and a reference electrode is provided opposite thereto on the reference air side. That invention is directed mainly to a reliable seal to ensure that no effects are exerted on the operation and performance of the two electrodes (sensor contacts) provided on the measurement gas side of the solid electrolyte. This construction makes possible a voltammetric measurement of two gas components in a gas mixture.

In addition, a gas sensor of the generic type is known from German published patent application DE 36 10 366 A1, in which a plurality of electrochemical measuring cells are arranged on a tubular support. This device allows only gaseous pollutants to be measured (not oxygen). The evaluation of the measurement signals takes place based on the characteristics of the pollutant concentrations.

Furthermore, a gas sensor of this type is known from German Patent DE 41 09 516 C2. In this device, the solid electrolyte is constructed in the shape of a platelet, on one side of which an electrode is applied which functions as a reference electrode, and on the opposite side of which at least two measuring electrodes are applied, which interact with various components of a gas mixture. The platelet-shaped sensor is built into a housing, which is then to be installed as a gas probe in the exhaust gas duct of a motor vehicle, more specifically perpendicular to the flow direction of the exhaust gas.

This probe functions without a reference gas, which is required for obtaining an electrode potential independent of the environment. However, such electrodes are not stable with respect to their electrochemical potential, especially when the mixture composition changes from lean to rich In addition, with configurations of the sensor design which are not rotationally symmetric, it is very hard to realize a stable and uniform temperature distribution over the entire surface. A similar, relatively complicated sensor is also known from German published patent application DE 42 43 734 A1.

SUMMARY OF THE INVENTION

In view of the above, an object of the present invention is to provide a gas sensor with which at least two gaseous components can be reliably detected simultaneously over a wide range of gas mixtures, and which also ensures a stable reference signal with the aid of ambient air, which additionally and, if necessary, allows the influence of the oxygen concentration by adding or removing oxygen at the respective measuring electrodes.

These objectives are achieved according to the present invention, wherein the solid electrolyte is constructed with one side exposed to the measurement gas and with a reference gas side separated from the measurement gas. The arrangement of the electrodes with the reference electrode on the reference gas side and with the at least two measuring electrodes on the measuring gas side is constructed such that one of the reference electrodes is assigned to at least one measuring electrode, which forms the anode of this electrode pair. The electrode pair is adapted to apply a voltage or a current for pumping of oxygen, and the arrangement simultaneously transmits at least two measurement signals, which correspond to different gaseous components. Alternatively, at least one of the reference electrodes can be assigned to at least two measuring electrodes, which are arranged spaced from one another on the same solid electrolyte.

According to the measurement method of the invention, oxygen is pumped from the reference gas side to the measurement gas side, whereby an oxygen excess is formed on the measurement gas side, and a difference signal is measured between two different measuring electrodes. Other advantageous amplifications of the invention, as well as the use of the gas sensor of invention, are described below and set forth in the dependent claims.

Advantageously the solid electrolyte, generally provided as a solid electrolyte body of virtually any desired shape, is constructed as a small tube closed at one end, which has on its inner wall a reference electrode, positioned as close as possible to the closed end, and a plurality of electrodes arranged on the outer side, exposed to the measurement gas. The solid electrolyte consists, e.g., of partially or fully stabilized $ZrO_2$ or of $CeO_2$. The arrangement of at least two independent measuring electrodes on the solid electrolyte guarantees the simultaneous detection of at least two measurement signals which correspond to at least two different gas components. Since a tubular solid electrolyte with a circular cross-section is used, the disturbances at an installation point perpendicular to the exhaust gas flow are thereby minimized, so that the measurement gas flows around the sensor in a relatively uniform manner. Accordingly, the gas components being measured arrive at the measuring electrodes practically without a delay, and the disturbing turbulence is avoided.

If the gas sensor is used at temperatures below 400° C., it is advantageous to provide the sensor with a heating element. The heating element for this purpose can be applied as a heating conductor, likewise on the outer side of the solid electrolyte, wherein, however, in order to avoid a short circuit, an electrically insulating layer is arranged between the heating conductor and the solid electrolyte.

Expediently, at least one of the electrodes used as a measuring electrode on the outer side of the solid electrolyte tube, closed at one end, is made of a catalytically active material, wherein different measuring electrodes can have different catalytically active materials. Consequently, the at least one measuring electrode is particularly suited for the potentiometric oxygen measurement according to the principle of a Nernst probe. In contrast, the second measuring electrode is made of a catalytically inactive material. This electrode is preferably used for detecting hydrocarbons.

It is advantageous if the surface of the measuring electrodes facing the measurement gas is covered with a preferably porous diffusion layer which, for example, can be made of aluminum oxide, spinel, or magnesium oxide, and which can have a different layer thickness over each measuring electrode, in order to be able to influence the oxygen residence time aimed at.

The reference electrodes assigned to the mutually spaced apart measuring electrodes can be divided into mutually spaced apart partial reference electrodes.

By using different catalytically active electrode materials for the adjacent measuring electrodes, assigned to the same reference electrodes, a gas-symmetrical differential measurement can be conducted between two measuring electrodes, wherein the selectivity with respect to hydrocarbons can be improved, for example by the choice of the oxygen pressure at these electrodes. At the same time, cross-influences arising through changing lambda are avoided. By the connection of a measuring electrode as the anode with respect to the reference electrode assigned to it, the targeted amount of oxygen can be pumped from the reference gas side to the measurement gas side by the application of a voltage or a current.

As catalytically active materials platinum or platinum alloys have proven satisfactory. Furthermore, rhodium or palladium are also suitable as catalytically active electrode materials. For the catalytically inactive materials, which should be used for the second measuring electrode, gold and gold alloys, as well as metal oxides have proven satisfactory. The catalytically inactive metal oxides are exemplified by mixed-conductivity perovskite compounds of the general formula $Ln_{1-z}A_{1-x}B_xO_3$, wherein Ln is a lanthanide cation, A is an element selected from the group Mn, Cr, Co, Fe, Ti, or Ni (preferably Cr or Ti), and B is an element selected from the group Ga, Al, Sc, Mg, or Ca.

By varying the composition of the measuring electrodes, it is possible to bring various gas components to the electrodes for interaction. The gas sensor according to the invention is therefore particularly suitable for applications for simultaneous measurement in gas mixtures where oxygen or lambda and hydrocarbons or carbon monoxide are to be found.

The measurement of oxygen is preferably carried out at the catalytically active measuring electrode, wherein the potential which arises, dependent on the concentration of oxygen in the measurement gas, is measured against the air reference electrode. This measuring electrode sets the measurement gas into equilibrium, and the voltage detected at this electrode gives a signal corresponding to that of known lambda probes.

At the measuring electrodes, which are preferably made of a catalytically inactive material, such as mixed-conductivity metal oxides (mixed-oxides), a voltage can likewise be detected against the (air) reference, which is determined from the concentration of unburned components, i.e., from the concentration of hydrocarbons or carbon monoxide in the exhaust gas.

In the method according to the invention, oxygen is pumped from the reference gas side to the side is exposed to the measurement, gas and a difference signal is measured between two different measuring electrodes.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiment(s) which are presently preferred. It should be understood, however, that the invention is not limited to the precise arrangements and instrumentalities shown. In the drawings.

DETAILED DESCRIPTION OF THE INVENTION

Figure 1:
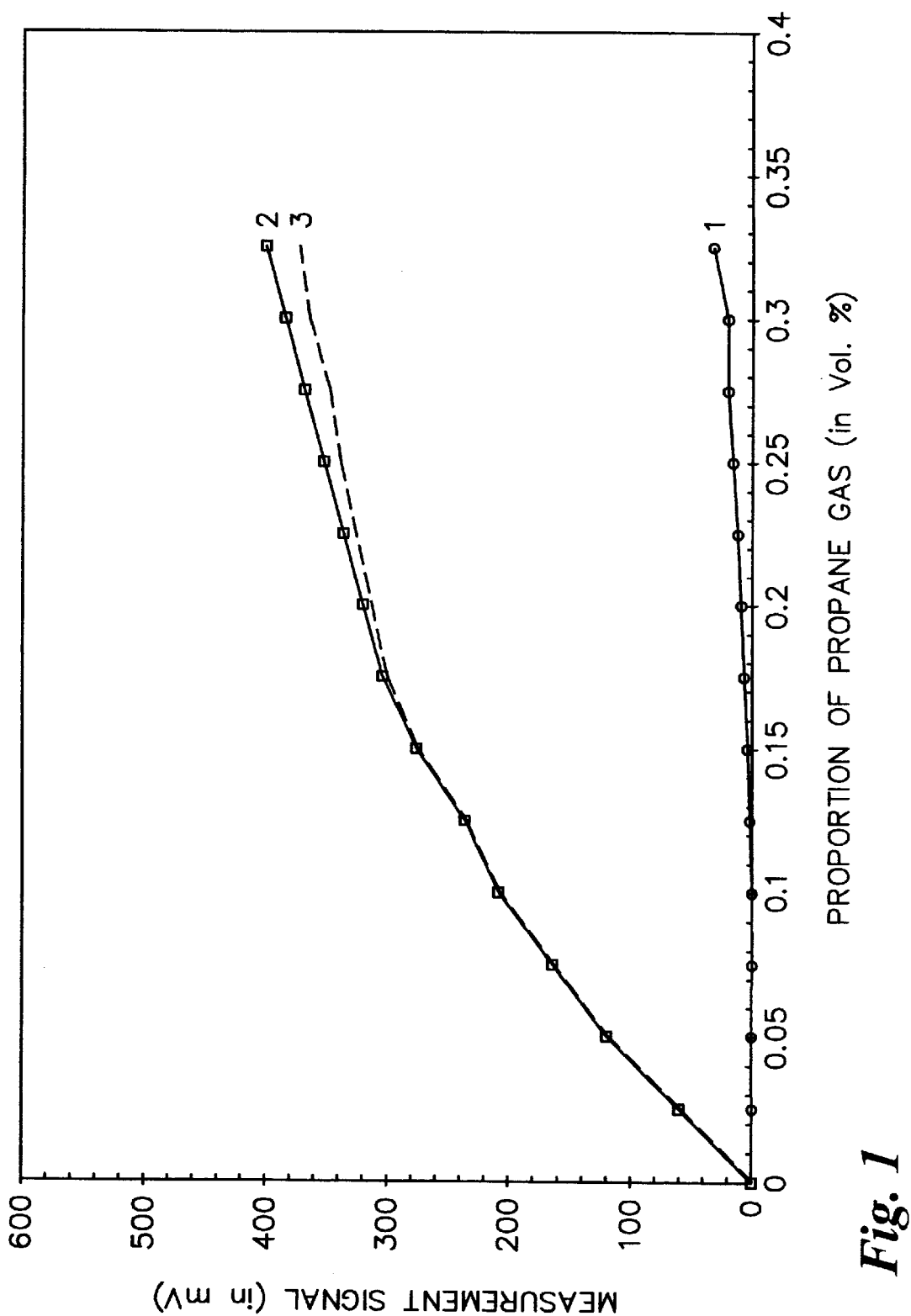
FIG. 1 is a set of characteristic curves of the measurement signals from a gas sensor of the invention according to FIG. 3, with a propane/oxygen measurement gas mixture.

FIG. 1 shows, by way of example, a set of characteristic curves of measurement signals obtained with the aid of a gas sensor of the invention. The sensor voltage in millivolts is plotted versus the propane gas concentration in volume %. Air is used as the reference gas. Curve 1 shows a measurement signal of the catalytically active platinum electrode; curve 2 represents a measurement signal of the catalytically inactive electrode (e.g., of gold); and curve 3 represents a difference signal between the two electrodes in a gas-symmetrical system.

Figure 2:
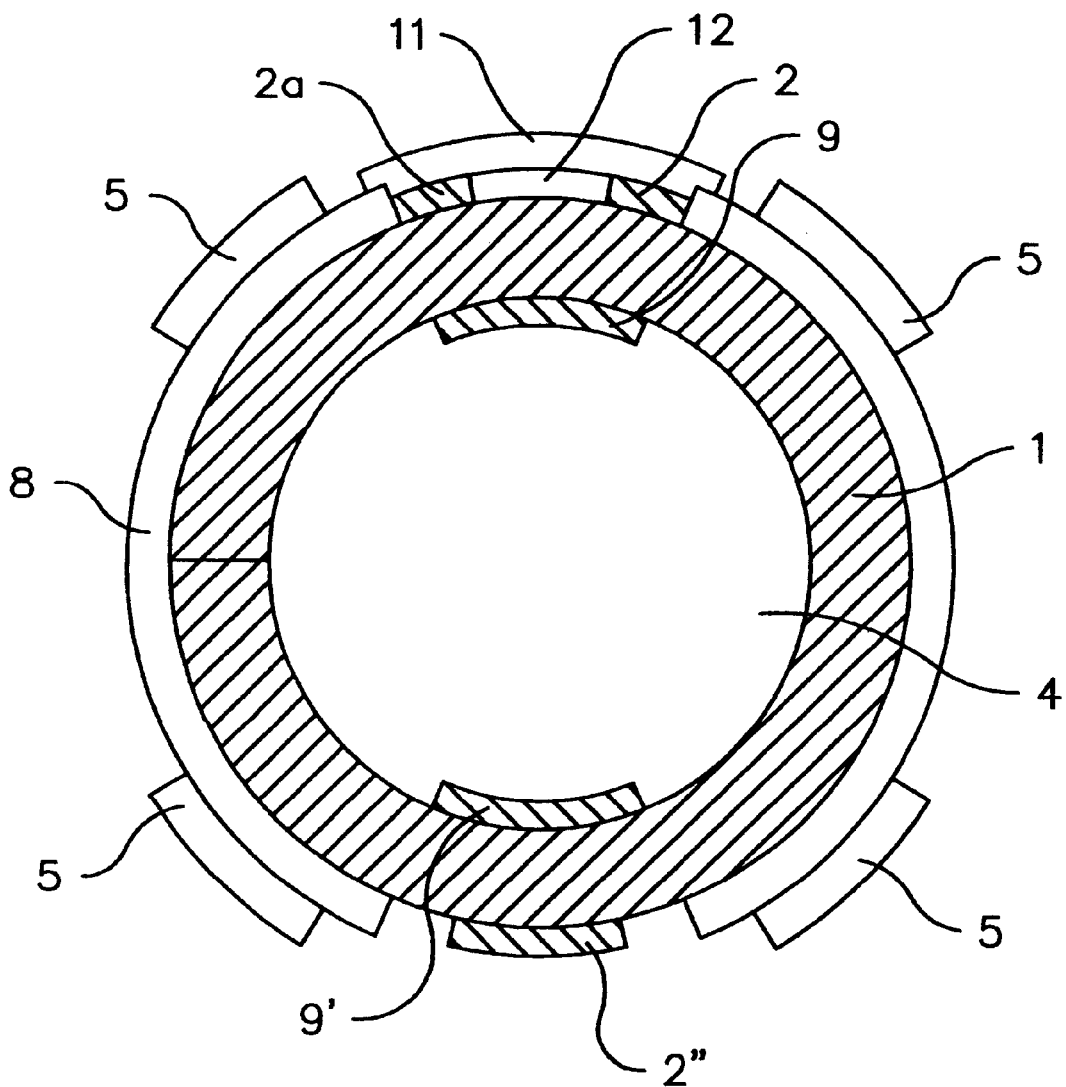
FIG. 2 is a sectional view through a tubular gas sensor of the invention for amperometric oxygen measurement and for potentiometric hydrocarbon measurement.

In FIG. 2 a sectional view is shown through a sensor according to the invention. A catalytically active electrode 2" is arranged on a tubular solid electrolyte 1 of $ZrO_2$, and opposite to it the reference electrode 9' is installed in the reference air passage 4. Further, an insulating layer 8 of $Al_2O_3$ is arranged on the outer side of the $ZrO_2$ tube 1, on which a heating element 5 is arranged symmetrically for a rapid heating of this gas sensor. Opposite to the measuring electrode 2" on the solid electrolyte 1 there are mounted two different catalytically active measuring electrodes 2, 2a of platinum or a platinum alloy, which are assigned to the reference electrode 9. Both measuring electrodes 2, 2a, for their part, are covered by a protective layer or a porous diffusion layer 11 of aluminum oxide. Aluminum oxide is provided as an insulating material 12 between the measuring electrodes 2 and 2a. Alternatively, spinel or magnesium oxide may be substituted for aluminum oxide as the insulating material 12.

With a surplus of oxygen, which arises by application of a voltage $U_{P1}$ between the electrodes 9 and 2a or $U_{P2}$ between the electrodes 9 and 2 and the thereby-generated pumping of oxygen into the measurement gas space, this construction of the gas sensor allows the hydrocarbon concentration or the carbon monoxide concentration to be determined gas-symmetrically or potentiometrically at two external electrodes 2, 2a. In this case, electrode pairs 9, 2 and 9, 2a can be coordinated to one another in an optimum manner. The high sensitivity achieved thereby can be influenced in a targeted manner by the heating elements 5, which are separately assigned to the electrodes 2, 2a. In the case of a divided construction of the reference electrode 9 as two partial reference electrodes, the sensitivity can be further increased. The solid electrolyte 1 is, for example, mounted in a housing in a manner well known to those skilled in the art, wherein the individual layers and electrodes can be electrically contacted, likewise in a known manner, for example at an end of the solid electrolyte 1.

Hydrocarbons are measured gas-symmetrically as a difference signal $U_2$ between the electrodes 2 and 2a, while between the electrodes 9' and 2" the voltage $U_1$ is measured as the oxygen signal with respect to the reference.

Figure 3:
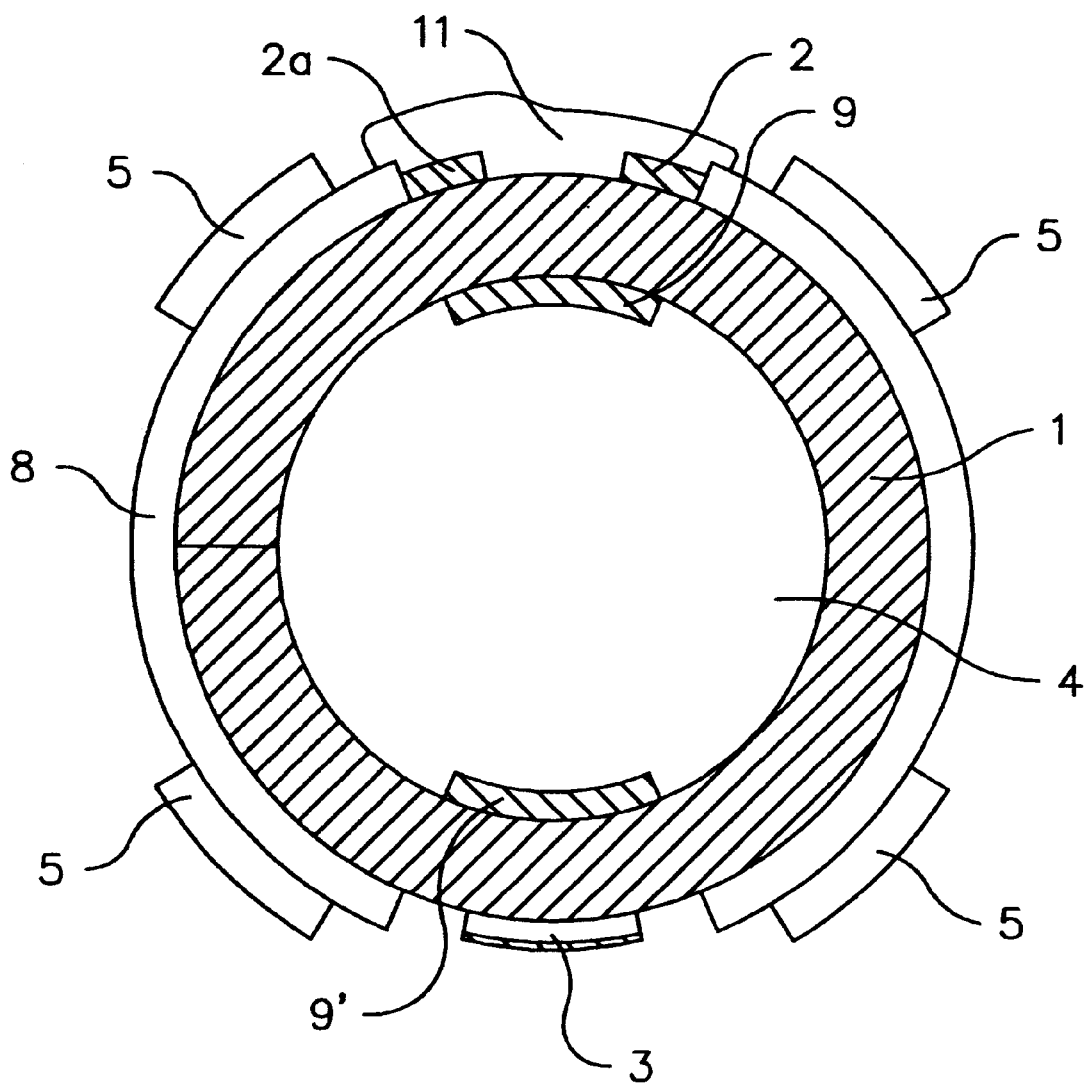
FIG. 3 is a sectional view through another embodiment of a tubular gas sensor of the invention for measurement of oxygen and hydrocarbons.

FIG. 3 shows, likewise in section, a tubular solid electrolyte 1 of $ZrO_2$. A catalytically inactive electrode 3, made of a perovskite material, and catalytically active electrodes 2, 2a, made of platinum or a platinum alloy, are applied on the outer side. The latter electrodes are covered with a porous diffusion layer 11 of $Al_2O_3$. This porous diffusion layer can have different thicknesses over the two electrodes 2, 2a. A reference electrode 9, 9' or counter-electrode 9' is arranged in the interior of the tube 1, respectively opposite the two measuring electrodes 2, 3. Similarly to FIG. 2, the gas sensor is provided with a heating element 5. The oxygen determination in this embodiment is carried out amperometrically by means of a pump current between the measuring electrode 2 and the reference electrode 9, which functions here as the counter-electrode. The hydrocarbon determination is carried out potentiometrically by measuring the voltage $U_3$ at the electrodes 9' and 3 or by the differential measurement $U_2$ between the electrodes 2 and 2a.

Figure 4:
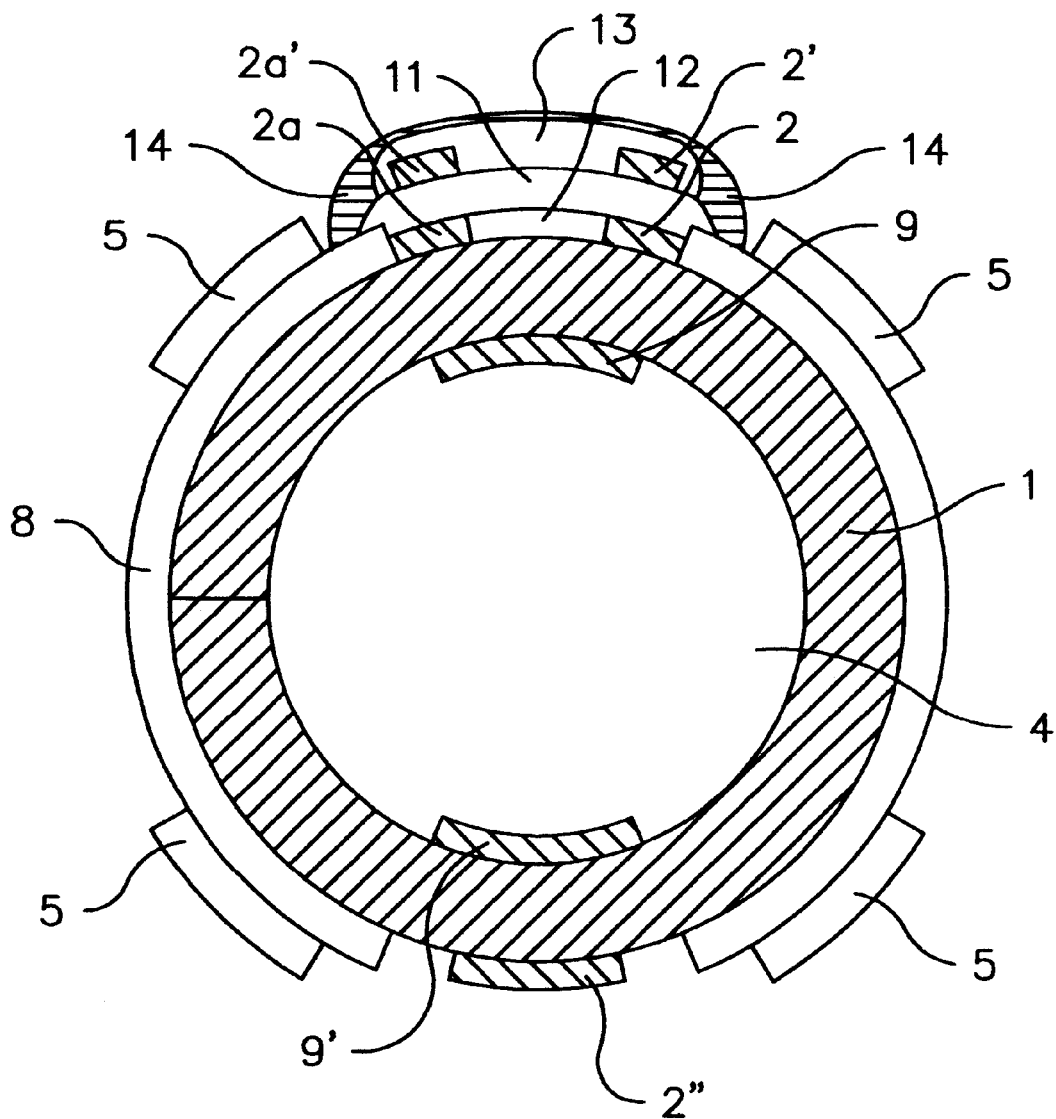
FIG. 4 is a sectional view through a tubular gas sensor of the invention for potentiometric measurement of oxygen and for amperometric measurement of oxygen and hydrocarbons.

FIG. 4 shows a sensor construction, similar to that depicted in FIG. 2, but additionally, further measuring electrodes 2', 2a' are arranged over the diffusion layer 11'. Here, the diffusion layer is also constructed as a solid electrolyte, so that an amperometric measurement with the pump current can be carried out between the measuring electrodes 2 and 9 or 2a and 9. The hydrocarbon determination is carried out by the differential measurement $U_2$ between the electrodes 2' and 2a'. The oxygen signal (potentiometric lambda determination) $U_1$ is measured between the electrodes 9' and 2". The two external electrodes 2', 2a' are covered with a porous oxygen ion-conducting material 13, which also extends over the intermediate space between these two electrodes 2', 2a'. The material 13 is covered by a gas-tight sealing layer 14, at least laterally until it extends onto the insulating layer 8, in order to rule out leakage of the measurement gas or oxygen.

It will be appreciated by those skilled in the art that changes could be made to the embodiment(s) described above without departing from the broad inventive concept thereof. It is understood, therefore, that this invention is not limited to the particular embodiment(s) disclosed, but it is intended to cover modifications within the spirit and scope of the present invention as defined by the appended claims.

We claim:

1. A gas sensor for measurement of oxygen and/or the air/fuel lambda ratio and hydrocarbons and/or carbon monoxide in a gas mixture, comprising at least one reference electrode representing a constant oxygen partial pressure, an oxygen ion-conducting solid electrolyte, and at least two measuring electrodes, the at least one reference electrode being mounted directly on the oxygen ion-conducting solid electrolyte and having electrical leads for connection and for take-away of at least two electrical measurement signals, each electrical signal corresponding to a different gaseous component of the gas mixture, wherein the oxygen ion-conducting solid electrolyte has a measurement gas side exposed to the gas mixture and a reference gas side separated from the gas mixture, wherein the at least one reference electrode is arranged on the reference gas side and the at least two measuring electrodes are arranged on the measurement gas side, wherein a single one of the at least one reference electrodes is operable with at least two of the measuring electrodes, the respective two measuring electrodes being spaced apart on the oxygen ion-conducting solid electrolyte, being covered with a porous diffusion layer and being exposed to the gas mixture, and wherein the porous diffusion layer has a different thickness over the respective two measuring electrodes and wherein the two measuring electrodes comprise the same catalytic activity.

2. The gas sensor of claim 1, wherein an insulating material selected from the group consisting of aluminum oxide, spinel and magnesium oxide is provided between the respective two measuring electrodes.

3. The gas sensor of claim 1, wherein a vacant space is provided between the respective two measuring electrodes.

* * * * *